United States Patent [19]

Ueno et al.

[11] Patent Number: 4,851,395
[45] Date of Patent: Jul. 25, 1989

[54] NITROGEN-CONTAINING POLYSACCHARIDE

[75] Inventors: Saburo Ueno, Tokyo; Chikao Yoshikumi, Kunitachi; Yoshio Omura, Tanashi; Takayoshi Fujii, Tokyo; Toshihiko Wada, Tochigi; Eiichi Takahashi, Kawaguchi; Fumio Hirose, Tokyo, all of Japan

[73] Assignee: Kureha Kagaku Kogyo Kabushiki Kausha, Tokyo, Japan

[21] Appl. No.: 163,238

[22] Filed: Feb. 26, 1988

Related U.S. Application Data

[60] Continuation of Ser. No. 801,392, Jun. 25, 1985, abandoned, which is a continuation of Ser. No. 558,711, Dec. 7, 1983, abandoned, which is a division of Ser. No. 96,209, Nov. 20, 1979, abandoned, which is a continuation-in-part of Ser. No. 788,892, Apr. 19, 1977.

[30] Foreign Application Priority Data

Jul. 7, 1976 [JP] Japan .................................. 51-80664

[51] Int. Cl.$^4$ ........................ A61K 31/73; C08B 37/00
[52] U.S. Cl. ........................................ 514/54; 536/1.1; 536/55.1
[58] Field of Search .................. 514/54; 536/1.1, 55.1

[56] References Cited

U.S. PATENT DOCUMENTS

| 2,146,873 | 2/1939 | Wilmann | 536/18 |
|---|---|---|---|
| 2,297,734 | 10/1942 | Wyler et al. | 536/18 |
| 3,207,663 | 9/1965 | Nomine et al. | 536/18 |
| 3,269,913 | 8/1966 | Devlin et al. | 536/18 |
| 3,301,848 | 1/1967 | Halleck | 536/18 |
| 3,422,085 | 1/1969 | Gill et al. | 536/18 |
| 3,956,272 | 5/1976 | Tixier | 536/18 |
| 4,051,314 | 9/1977 | Ohtsuka et al. | 536/1.1 |
| 4,140,578 | 2/1979 | Yoshikumi et al. | 536/55.1 |
| 4,202,885 | 5/1980 | Asano et al. | 536/1 |
| 4,202,969 | 5/1980 | Ueno et al. | 424/181 |
| 4,228,275 | 10/1980 | Asano et al. | 536/55.1 |
| 4,229,570 | 10/1980 | Ueno et al. | 536/1 |
| 4,678,773 | 7/1987 | Usami et al. | 536/17.1 |
| 4,689,222 | 8/1987 | McMichael | 424/88 |
| 4,692,332 | 9/1987 | McMichael | 424/88 |
| 4,698,422 | 10/1987 | Hill et al. | 536/17.1 |

OTHER PUBLICATIONS

Johnson et al., "Cancer Treatment Reviews", 1975, 2, pp. 1–8.

Primary Examiner—Ronald W. Griffin
Attorney, Agent, or Firm—Wegner & Bretschneider

[57] ABSTRACT

Disclosed is nitrogen-containing polysaccharide substantially free of units having a molecular weight below about 5,000, said nitrogen-containing polysaccharide having been extracted from Coriolus versicolor (Fr.) Quel., substantially all polymer units having a molecular weight below about 5,000 having been removed therefrom, which exhibits antitumor and immunological activity.

3 Claims, 1 Drawing Sheet

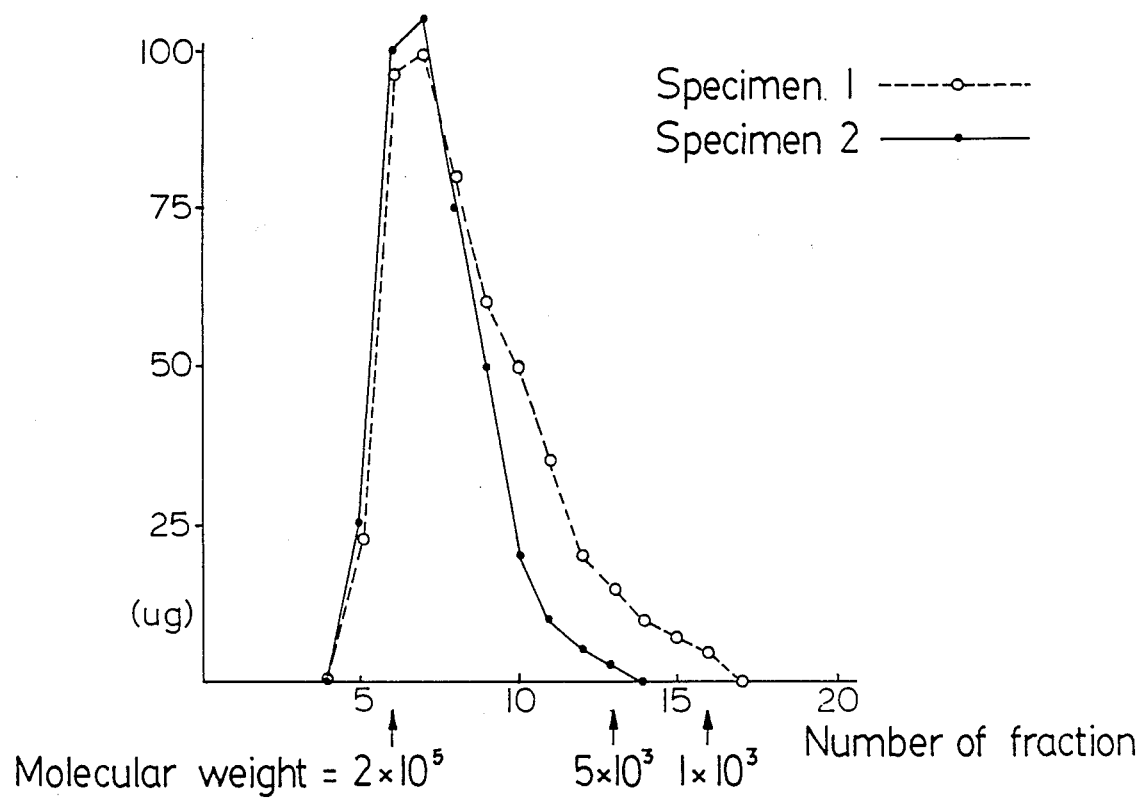

NITROGEN-CONTAINING POLYSACCHARIDE

CROSS-REFERENCE TO RELATED APPLICATIONS

This application is a continuation of Ser. No. 801,392, filed Nov. 25, 1985, now abandoned which is a continuation of Ser. No. 558,711, filed Dec. 7, 1983, now abandoned, which is a divisional of Ser. No. 96,209, filed Nov. 20, 1979, now abandoned, which is a continuation-in-part of Ser. No. 788,892, filed Apr. 19, 1977.

SUMMARY OF THE INVENTION

In a first aspect of the invention, there is provided a nitrogen-containing polysaccharide substantially free of units having a molecular weight below about 5,000, said nitrogen-containing polysaccharide having been extracted from *Coriolus versicolor* (Fr.) Quél., substantially all polymer units having a molecular weight below about 5,000 having been removed therefrom.

In a second aspect of the invention, there is provided a method of restoring the immune response of a patient having a lowered immune response level which comprises administering to said patient a nitrogen-containing polysaccharide substantially free of units having a molecular weight below about 5,000, said nitrogen-containing polysaccharide having been extracted from *Coriolus versicolor* (Fr.) Quél., substantially all polymer units having a molecular weight below about 5,000 having been removed therefrom.

In a third aspect of the invention, there is provided a method of inhibiting the growth of cancer cells in a patient afflicted therewith which comprises administering to said patient a nitrogen-containing polysaccharide substantially free of units having a molecular weight below about 5,000, said nitrogen-containing polysaccharide having been extracted from *Coriolus versicolor* (Fr.) Quél., substantially all polymer units having a molecular weight below about 5,000 having been removed therefrom.

In a fourth aspect of the invention, there is provided an antimumor agent suitable for inhibiting the growth of cancer cells in a patient afflicted therewith which comprises as an active ingredient a nitrogen-containing polysaccharide substantially free of units having a molecular weight below about 5,000, said nitrogen-containing polysaccharide having been extracted from *Coriolus versicolor* (Fr.) Quél, substantially all polymer units having a molecular weight below about 5,000 having been removed therefrom.

BRIEF EXPLANATION OF DRAWING

The drawing shows the molecular weight distribution curves of polysaccharide specimens 1 and 2 described in Example 1, taking the number of fraction arranged in the inverse order of molecular weight in the abscissa, and the weight of each fraction in the ordinate. While circles and a dotted line represent the molecular weight distribution of the extract of *Coriolus versicolor*(Fr.)Quél. with an aqueous 0.1N sodium hydroxide solution, i.e., Specimen 1, black dots and a solid line represent that of the product of the present invention, i.e., Specimen 2 obtained by refining the above-mentioned extract to remove the substance having molecular weight of less than 5,000.

DETAILED DESCRIPTION OF THE INVENTION

The fungus used as the starting material in the present invention is *Coriolus versicolor* (Fr.) Quél. *Coriolus versicolor* (Fr.) Quél. is now a well known fungus, disclosed in the 1960's in Japan. E.g., note Example 22 of U.S. Pat. No. 4,051,314. Samples of two strains suitable for the present invention are FERM-P 2414 and FERM-P 2412, which are available to the public under their accession numbers from the Fermentation Research Institute, Agency of Industrial Science and Technology (Chiba-shi, Japan), a part of the Japanese government designated by the Director-General of the Japanese Patent Office for the filing of microorganism cultures to be referred to in patent applications. Although a fruit body of the fungus may be used, it is preferable to use a mycelium obtained by the artificial culture of *Coriolus versicolor* (Fr.) Quél.

A method of producing the nitrogen-containing polysaccharide of the present invention is characterized by the steps of extracting the above-mentioned fungus with a 0.01N to 2N aqueous alkaline solution and subjecting the thus obtained extract to ultrafiltration and/or reverse osmosis to remove the low molecular weight components having a molecular weight of less than 5,000 from the extract.

The concentration of the alkaline solution used for the extraction of the fungus in the present invention should be in the range of 0.01N to 2N because when it is less than 0.01N, the result is not so much different from that obtained by extraction with water, while when it exceeds 2N, there may be some decomposition of the product. Preferable extraction of the fungus can be accomplished by using an alkaline solution with a concentration in the above-mentioned range at a temperature of 50° to 100° C., preferably 80° to 98° C., for a period of 20 to 600 minutes. It should be noted that the extraction performed at a temperature of lower than 50° C. results in insufficient extraction of the active component, while the extraction performed at a temperature of over 100° C. may cause the reduction of the activity of the obtained active component. The preferable range of the time period of the extraction depends on the concentration and the temperature of the alkaline solution used; however, usually it is preferable to extract for 20 to 600 minutes as is mentioned above. It is possible to obtain a satisfactory result with a single extraction, however, if desired, extraction may be repeated several times.

Various kinds of alkaline substances, such as sodium hydroxide, potassium hydroxide, aqueous ammonia and calcium hydroxide, etc. may be used for the alkaline solution in the present invention. The use of sodium hydroxide or potassium hydroxide is more preferable.

The aqueous extract obtained in the above-mentioned procedure is neutralized by a mineral acid such as diluted hydrochloric acid and then subjected to ultrafiltration or reverse osmosis to remove the substances with molecular weight of less than 5,000 contained in the extract.

A prominent feature of the refining means used in the present invention is that the component substances are fractionated under pressure according to their molecular weights by using a membrane which may be termed a kind of molecular sieve. In such fractionation by the membrane, the molecular weights are usually determined according to the kinds of the membrane used;

however, since the performance of fractionation depends greatly on both the molecular weight and the configuration of molecules in a solution in which these molecules are dissolved, the values of molecular weight of the fractions indicated in the catalogue supplied by the producer of commercialized membranes for ultrafiltration and the generally applicable environmental conditions are not always applicable to the refining of the extract according to the present invention. In this respect, it was confirmed that a membrane bearing the indication of the producer of 5,000 to 15,000 of the fractioned molecular weight and effective in inhibiting the passage of cytochrome C of molecular weight of 13,000 at 98 to 100% is suitable for use in the present invention.

The operation of the ultrafiltration of the present invention is carried out usually under a pressure of 0.5 to 5 kg/cm$^2$, preferably 1 to 4 kg/cm$^2$, and at a temperature of usually 5° to 70° C. although the operation temperature may vary depending on the type of membrane. In the case of operation of reverse osmosis, the pressure applied is usually within the range of 20 to 35 kg/cm$^2$, preferably 20 to 25 kg/cm$^2$ and the temperature at the operation is usually within the range of 5° to 20° C.

Generally, it is considered that ultrafiltration is suitable for fractionation of material with molecular weight of over 10,000, while reverse osmosis is suitable for fractionation of material with molecular weight of less than 1,000. Fractionation for cutoff of molecules with molecular weight less than 5,000, which is the intention of the present invention, is intermediate of the ranges recommended for the above-mentioned two respective methods. However, it was revealed that both methods can be applied in fractionation of the substances with molecular weight less than 5,000 by suitable selection of the membrane. Therefore, in refining the extract according to the method of this invention, the ultrafiltration and reverse osmosis methods may be used either singly or in combination, and such selection is made by taking into consideration workability and operating efficiency.

The extract from which the substances (with molecular weight of less than 5,000) have been removed by the above-mentioned refining operation is subjected to spray-drying or freeze-drying and is thereafter suitable for incorporation in pharmaceutical preparations.

The substance obtained in the above-described manner according to the present invention is liver brown in color and has a nitrogen content of from 2 to 8%, in many cases 3 to 6%. It exhibits no distinct melting point and is gradually blackened and decomposed at a temperature of higher than about 120° C. As for solubility of the substance of this invention, it is soluble in water but almost insoluble in alcohol, pyridine, chloroform, benzene and hexane. It is also tasteless and odorless.

Various color reaction tests on the substance obtained according to the method of the present invention gave the results as shown in Table 1 below.

TABLE 1

| (Color reaction tests) | | | |
|---|---|---|---|
| | Color | Results | |
| α-naphthol sulfuric acid reaction (Molish's reaction) | Purple | Saccharides | Confirmed |
| Indole sulfuric acid reaction (Disch's reaction) | Brown | Saccharides | Confirmed |
| Anthrone sulfuric acid reaction | Greenish blue | Saccharides | Confirmed |
| Phenol sulfuric acid reaction | Brown | Saccharides | Confirmed |
| Tryptophane sulfuric acid reaction | Purplish brown | Saccharides | Confirmed |
| Lowry-Folin process | Blue | Peptide bonds | Confirmed |
| Ninhydrin reaction after hydrochloric acid hydrolysis | Greenish blue | α-amino acids | Confirmed |

The results shown in the above table imply that the substance of the present invention (hereinafter referred to as the present substance) is a nitrogen-containing polysaccharide. The molecular weight of the present substance, as measured according to an ultra-centrifugal method, ranged from 5,000 to 300,000 and the weight-average molecular weight ranged from 10,000 to 100,000. Other measuring methods, such as fractionating by use of an ultrafiltration membrane, also gave the values of 10,000 to 100,000. Therefore, it may be estimated, with high reliability, that the average molecular weight of the present substance is within the range of 10,000 to 100,000.

The nitrogen-containing polysaccharide of the present invention not only demonstrated a high anti-tumour activity with high inhibition ratio against Sarcoma-180 solid tumor in mice in intra-peritoneal administration but also proved effectiveness in oral administration. This is indicative of very high availability of the nitrogen-containing polysaccharide of the present invention as an oral anti-tumour agent, and in fact, such effect has been confirmed in various experiments. Use of the present substance is not limited to such oral anti-tumour medications; it also shows a high activity of preventing the decline of immunity and a high activity of recovering the declined immunity both in humans. That is, it is effective not only for prevention of side actions in chemotherapy of cancer or increase of sensitivity of tumors against ionizing radiation in radio-therapeutics but also for prevention of decline of immunity and physical strength of the patient after an operation or blood transfusion and control or protection against infectious diseases caused by virus or bacteria due to decline of immunity or physical strength. Oral administration of the present substance also produced an excellent effect in improvement of liver function, increase of appetite, adjustment of intestinal disorders and promotion of urination.

Although oral administration is preferred, other modes, e.g., parenteral may be used. For oral administration a powder is preferred, although other forms may also be used, e.g., tablets, granules, capsules and syrups. Although a substantially pure powder of the nitrogen-containing polysaccharide is used in a preferred embodiment, diluents may optionally be included.

It is to be understood that the nitrogen-containing polysaccharide of the present invention may be used either alone or in admixture with other active ingredients. For example, there has recently been used "cocktails" of various drugs, including painkillers, tranquilizers, anti-tumor drugs, vitamins, antibiotics, digestives, anti-inflammatory drugs and hormones, for terminally ill cancer patients at hospices specifically designed for such terminally ill patients. Due partially to the extremely low toxicity of the nitrogen-containing polysaccharide of the present invention, it may be used in admixture with the other ingredients of such "cocktails".

It is contemplated that for immune response and tumor treatment that from about 0.5 to about 30 g per adult per day, is orally administered, and more preferably from about 1 to about 6 g per day.

When the nitrogen-containing polysaccharide is utilized according to a preferred embodiment, approximately 1 g is taken orally three times per day, the nitrogen-containing polysaccharide being a substantially pure powder which is stirred quickly into a glass of water and then taken by the patient.

The nitrogen-containing polysaccharide of the present invention demonstrated an excellent anti-tumor activity as well as other pharmacodynamic effects such as above-mentioned not only in intra-peritoneal administration but also in oral administration as mentioned in the following embodiments.

EXAMPLE 1

The present Example shows the difference between the extract of the fungus, Coriolus versicolor (Fr.) Quél. with an aqueous alkaline solution and the nitrogen-containing polysaccharide of the present invention, i.e., the refined product obtained from the above-mentioned extract by removing the substance having molecular weight less than 5,000 from the above-mentioned extract, particularly in (1) molecular weight distribution (2) anti-tumor activity and (3) immunological activity in stimulating the blastogenesis of human lymphocytes.

(1) Molecular weight distribution:

The specimens of nitrogen-containing polysaccharides for the determination of molecular weight distribution were obtained by an ordinary procedure.

Accordingly, the following three specimens were obtained:

(i) specimen 1: the substance consisting of polysaccharides of all range of molecular weights as far as possible, obtained by de-salting with hollow filaments the raw extracted material prepared by an ordinary procedure of extraction.

(ii) specimen 2: the substance consisting of polysaccharides of molecular weight of higher than 5,000 which was obtained by an ordinary procedure, by removing the substance of molecular weight of lower than 5,000.

(iii) specimen 3: the substance consisting of substances of molecular weight of lower than 5,000. The substance was obtained by collecting the substance removed by the procedures of (ii) as those of molecular weight of lower than 5,000 and by de-salting the thus collected substance.

Of these three specimens, two specimens 1 and 2 were subjected to the determination of molecular weight distribution. At first, each specimen was partitioned to fractions by gel-chromatography using Sephadex G-200-foiled column and each fraction obtained by the chromatography was subjected to colour reaction in the phenol-sulfuric acid method. The colouration due to polysaccharide was translated into the weight-molecular weight relationship (molecular weight distribution) and the results were illustrated in FIGURE. In the FIGURE, the abscissa denotes the molecular weight (inverse direction) and the ordinate denotes the amount in weight.

Conditions for Gel Chromatography for determining Molecular Weight Distribution of Specimens 1 and 2.

Stational phase in the column: Sephadex G-200
Size of the column: $1 \times 50$ cm
Eluant: water
Volume of one fraction: 3 ml
Method of determination: Phenol-sulfuric acid method of colorimetry.
Specimens: Specimen 1 shown by circles and a dotted line Specimen 2 shown by black dots and a solid line Specimen 1:

Two hundred grams of dried mycelia of Coriolus versicolor (Fr.)Quél. (FERM-P No. 2412) moisture content: 8.8% and gross nitrogen content: 2.5%) were put into 4 liters of aqueous 0.1N NaOH solution and extracted under agitation in a boiling water bath at internal temperature of 90° to 95° C. for one hour, and then the mixture was cooled to a temperature of below 50° C. and aqueous 1N HCl solution was gradually added to the cooled mixture to adjust its pH to 7.0. Then the solids in the mixture were removed by suction filtration and these solids were washed with 500 ml of water to obtain 4.2 liters of liquid extract in all. This liquid extract was then subjected to dialysis, by using hollow fibers (HFO, registered trade name of Dow Chemical Co., U.S.A.) to remove salts therein, followed by concentration to obtain 300 ml of processed solution. By freeze-drying the concentrate, about 35.5 g of a powder liver-brown in colour were obtained.

Specimen 2:

Two hundred grams of dried mycelia of Coriolus versicolor(Fr.) Quél. (FERM-P No. 2412) (moisture content: 8.8% and gross nitrogen content: 2.5) were put into 4 liters of aqueous 0.1N NaOH solution and extracted under agitation in a boiling water bath at internal temperature of 90° to 95° C. for one hour, and then the mixture was cooled to a temperature of below 50° C. and aqueous 1N HCl solution was gradually added to the cooled mixture to adjust its pH to 7.0. Then the solids in the mixture were removed by suction filtration and these solids were washed with 500 ml of water to obtain 4.2 liters of liquid extract in all. After dialysis this liquid extract was then subjected to ultrafiltration under agitation and cooling and under operating pressure of 1.5 kg/cm$^2$ at 10° C. to remove low molecular weight substances with molecular weight of less than 5,000, followed by concentration to obtain 300 ml of processed solution. This solution was further subjected to freeze-drying to obtain about 26.6 g of liver brown-coloured powder.

Specimen 3:

The filtrate of ultrafiltration obtained by the precedent procedure for obtaining Specimen 2 was collected and it was de-salted with hollow fibers. Upon freeze-drying the de-salted filtrate, a powdery substance was obtained.

(2) Anti-tumor effect:

Anti-tumor effect of the above-mentioned three specimens was determined by the following method, and shown in Table 2.

Anti-tumor test method

The anti-tumor effect of the specimens 1, 2 and 3 was determined according to an ordinary method which is briefly described below.

Sarcoma-180 tumor cells were transplanted in the abdominal cavity of a mouse, and after allowing sufficient growth of the cells for the period of 7 days, 10$^6$ of these cells were further transplanted under the skin of the axilla of each mouse of two groups to form solid tumors. Intra-peritoneal administration of each specimen was started from 24th hour after transplantation at the dose of 10 mg/kg per administration once every other day for 20 days. The tumors were enucleated on 25th day after transplantation, and the tumor growth inhibition ratio was calculated from the average tumor weight T in the mice to which each specimen was administered and the average tumor weight C in the control mice (transplanted, however, not administered) as follows:

Anti-tumor effect = tumor growth inhibition ratio = I.R.

$$I.R. = \left(1 - \frac{T}{C}\right) \times 100$$

I.R. being presented by percentage.

TABLE 2

| No. | Specimen | I.R. (%) |
| --- | --- | --- |
| 1 | Specimen 1 | 67 |
| 2 | Specimen 2 | 90 |
| 3 | Specimen 3 | 0 |

Results abstracted:

As seen in Table 2, Specimen 3 consisting of molecules with molecular weight lower than 5,000 did not show any anti-tumor effect.

Specimen 1 which is considered to consist of Specimen 2 and the inactive Specimen 3 is a little effective, however, its effectiveness is far inferior to the effectiveness of Specimen 2.

(3) Comparison of biological activities of the fractions of the polysaccharide obtained by extracting a fungus *Coriolus versicolor*(Fr.)Quél. on the blastogenesis of human lymphocytes in vitro.

The polysaccharide obtained from fungal bodies of *Coriolus versicolor*(Fr.)Quél. not being fractioned showed a fairly high stimulating activity on the blastogenesis of human lymphocytes; however, a fraction of the same polysaccharide having a molecular weight less than 5,000 did now show such a stimulating activity. The remaining fraction of the polysaccharide having a molecular weight of more than 5,000, i.e., the product of the present invention, showed the highest activity in stimulating the blastogenesis of human lymphocytes of the three specimens tested, as has been estimated. The test results are shown in Table 3:

TABLE 3:

| Stimulant | Stimulation of the blastogenesis of human lymphocyte | |
| --- | --- | --- |
| | Uptake of $^3$H—TdR(cpm)* | Stimulation Index |
| — | 340 ± 105 | 1 |
| Specimen 1 | 4220 ± 610 | 12.1** |
| Specimen 2 | 7003 ± 1295 | 20.1** |
| Specimen 3 | 456 ± 171 | 1.3 |

Notes: *Values are means cpm with standard deviation.
**P < 0.01
Specimen 1: intact specimen, not fractioned.
Specimen 2: having molecular weight of more than 5,000.
Specimen 3: having molecular weight of less than 5,000.

Materials and Methods:

Lymphocyte Culture: Venous blood from healthy adult donors was defibrinated with glass beads. Lymphocytes were isolated on a layer of Ficoll-Conray by one centrifugation at 400 g for 30 min. The cell suspension obtained contained less than 2% neutrophils but monocytes were not eliminated. Lymphocytes were cultured by a microculture method. A mixture of $15 \times 10^4$ lymphocytes in 0.2 ml of RPMI-1640 medium supplemented with 20% fresh human AB serum was placed in each well of a microplate (Microtest II, Falcon Plastics, Oxnard. U.S.A.) and incubated in humidified atmosphere with 5% $CO_2$ at 37° C. All experiments were performed in quadruplicate cultures. These substances were added to the culture in a volume of 0.02 ml at the beginning of the cultivation.

Measurement of DNA Synthesis of Cultured Lymphocytes:

To measure the rate of DNA synthesis of the cultured lymphocytes, 0.02 micro Ci of $^3$H-thymidine ($^3$H-TdR, New England Nuclear, Boston, U.S.A. spec act, 11.5 Ci/mmol) was added to each culture on the last day of the cultivation. The cultures were incubated for 7 hours more and harvested using the Multiple Automated Sample Harvester II (MASH II, Microbiological Assoc., Washington, U.S.A.). After the harvesting procedures, the filter strips were placed and dried in counting vials to which 8 ml of toluene containing 0.5% PPO and 0.01% POPOP was added. The incorporated radioactivity was counted in a liquid scintillation counter (LS-335, Beckman Instrument Inc., Fullerton, U.S.A.). The counts were expressed as cpm/$10^6$ lymphocytes during 1-hour incubation with $^3$H-TdR. The stimulation index was determined by dividing the counts in the stimulated cultures by the counts in the unstimulated cultures.

Results:

The nitrogen-containing polysaccharide fraction having a molecular weight of more than 5,000, i.e., the product of the present invention, stimulated human peripheral lymphocytes from adult healthy donors at the concentration of 1 mg/ml. The stimulation index after 5 days in culture was: a mean value of 20.1, at the concentration of 1 mg/ml. The stimulatory effect of the substance at the concentration of 1 mg/ml was statistically significant (P<0.01).

On the other hand, the polysaccharide fraction having a molecular weight of less than 5,000 did not show such a stimulatory effect.

EXAMPLE 2

200 g of dry mycelia of *Coriolus versicolor*(Fr.)Quél. (FERM-P-No. 2414) (moisture content: 8.8%; gross nitrogen content: 2.5%) was added in 4 liters of 0.1N NaOH solution and extracted under agitation in a boiling water bath at internal temperature of 90° to 95° C. for one hour, and then the mixture was cooled to a temperature of below 50° C. and gradually admixed with 1N HCl solution to adjust pH to 7.0. Then the solids were removed by suction filtration and these solids were washed with 500 ml of water to obtain 4.2 liters of liquid extract in all. This liquid extract was then subjected to ultrafiltration, by using a desk-top ultrafilter by Amicon Inc. (ultrafiltration membrane: PM-5), under agitation and cooling with an operating pressure of 1.5 kg/cm$^2$ at 10° C. to remove low molecular weight substances with molecular weights of less than 5,000, followed by concentration to obtain 300 ml of processed solution. This solution was further subjected to freeze-drying to obtain about 26.6 g of a liver brown powder (yield: 13.5%). This powder had a moisture content of 7.5% and elemental analysis thereof gave the following composition: C: 40.5%; H: 6.2%; N: 5.8%; O: 47.5%. (The percent of oxygen is the value obtained by subtracting the total percent of other elements from 100). It was eaily soluble in water. Also, it showed as high as 90% inhibition ratio against Sarcoma-180 solid tumour in mice in intra-peritoneal administration and 65% inhibition ratio in oral administration.

The anti-tumour effect of the products according to this invention was determined according to an ordinary method which is briefly described below.

Sarcoma-180 tumour cells were transplanted in the abdominal cavities of mice, and after allowing growth of the cells for a period of 7 days, $10^6$ of these cells were further transplanted under the skin of the axilla of other mice to form solid tumours. Administration of the product to be tested was started from 24th hour after transplantation. In the case of intra-peritoneal administration, the product was administered in a dose of 10 mg/kg per administration once every other day for 20 days for a total dosage of 0.2 ml per 20 g of mouse body weight, and in the case of oral administration, the product was administered in a dose of 1000 mg/kg per administration once a day for 20 days for a total dosage of 0.2 ml per 20 g of mouse body weight. The tumours were enucleated on the 25th day after transplantation, and the tumour growth inhibition ratio was calculated from the average tumour weight in the mice to which the product of this invention was administered and the average tumour weight in the control mice. For the sake of comparison, the extraction and refining treatment was performed under the same conditions but by using water instead of 4 liters of 0.1N NaOH solution. The product yield was 7.8%, or about 60% of that attained with the method of this invention.

EXAMPLE 3

500 g of living mycelia of *Coriolus versicolor*(Fr.) Quél. (FERM-P No. 2414) (moisture content: 70.8%; gross nitrogen content: 2.6% calculated on the dry base) mixed in 2 liters of water and ground by a juice mixer for 10 to 20 minutes, and the mixture was then gradually admixed with 500 ml of 1N-NaOH solution and extracted in a hot water bath at 90° to 95° C. for 2 hours, followed by neutralization with HCl, washing and separation of cells according to the procedure of Example 2. The obtained extract was subjected to ultrafiltration by using a desk-top ultrafilter (ultrafiltration membrane: G-05T membrane by Bio-Engineering Co.) to eliminate the low molecular weight substances of a molecular weight of less than 5,000, followed by concentration and freeze-drying to obtain 24.2 gr of liver brown powder (yield: 15.1%). This powder was 7.6% in moisture content and 6.0% in gross nitrogen content and had insoluble portion of approximately 20% when dissolved in water. The remaining portion was easily soluble in water. (Elementary analysis showed C: 41.2%; H: 6.1%; N: 6.0%; O: 46.7% (percent of oxygen being the value obtained by substracting the total of C, H and N values from 100)). This powder was dissolved and, after removing the insolubles by a filter paper (No. 5c), its inhibitory action against Sarcoma-180 solid tumour in mice was examined. It showed as high as 93% inhibition ratio in the case of intra-peritoneal administration and 70% inhibition ratio in the case of oral administration.

EXAMPLE 4

2 kg of dry cells of *Coriolus versicolor*(Fr.)Quél. (FERM-P No. 2414) (moisture content: 8.0%, gross nitrogen content: 2.5%) were placed in 20 liters of 0.4N NaOH solution and subjected to 2-hour extraction under agitation in an extraction vessel equipped with a heating-cooling jacket and an agitator while regulating the jacket temperature so that the internal temperature stayed at 90° to 95° C. The extracted slurry was cooled down to room temperature and, after adjusting pH to 7.0 by adding 2N-HCl portionwise with agitation, the residue (solids) was separated from the liquid extract by a centrifugal separator. The residue (solids) was mixed with 20 liters of 0.4N-NaOH solution and subjected to a similar extraction treatment at 90° to 95° C. for 2 hours, followed by cooling, neutralization and centrifugal separation (separation of cells) to obtain liquid extract and the residue. The latter was once again subjected to a similar extraction treatment with 0.4N-NaOH solution for one hour to obtain an extract. This three-times repeated extraction operation gave about 58 liters of liquid extract in total. This liquid extract was concentrated to approximately 10 liters by a vacuum concentrator and then treated in an ultrafilter (using HFA-180 Membrane by Abcor Inc.) at 10° C. and under 30 psi to remove the low molecular weight substances (with molecular weight of less than 5,000), followed by additional concentration to obtain approximately 5 liters of processed solution. Then, about 70 liters of the solution containing the low molecular weight fraction discharged from the ultrafilter was subjected to a reverse osmoser (using AS-205 membrane by Abcor Inc.) to remove the low molecular weight substances and then concentrated to obtain approximately 5 liters of processed solution. The operating conditions used for this treatment were as follows: average pressure: 25–30 kg/cm$^2$; treating temperature: about 10° C. Then the solutions obtained from the ultrafiltration and reverse osmotic treatment were put together and the 10 liters of the combined solution spray-dried to obtain about 395 g of liver brown powder (yield: 19.9%). This powder had a moisture content of 7.0% and its elemental analysis gave the following results: C: 40.8%; H: 6.0% N: 4.0% O: 49.2%. The inhibition ratio of this product against Sarcoma-180 solid tumor in mice was 92% in the case of intra-peritoneal administration and 70% in the case of oral administration. It was easily soluble in water.

What is claimed is:

1. A nitrogen-containing polysaccharide substantially free of units having a molecular weight below about 5,000, said nitrogen-containing polysaccharide having a nitrogen content of from 3 to 8%, showing positive results when subjected to the Molish's reaction, the Disch's reaction, the anthrone sulfuric acid reaction, the phenol sulfuric acid reaction, the tryptophane sulfuric acid reaction, the Lowry-Foline reaction and the ninhydrin reaction after hydrochloric acid hydrolysis, and being a product produced by extracting *Coriolus versicolor* (Fr.) Quel. with an aqueous alkaline solution having a concentration within the range of from 0.01 to 2.0N at a temperature of from 50° C. to 100° C., neutralizing the resultant extract, and subjecting the resulting neutralized extract to ultrafiltration or reverse osmosis to remove substantially all polymer units having a molecular weight below about 5,000 therefrom.

2. A method of inhibiting the growth of tumor cells in a patient suffering therefrom comprising administering to said patient a nitro-containing polysaccharide substantially free of units having a molecular weight below about 5,000, said nitrogen-containing polysaccharide having a nitrogen content of from 3 to 8%, showing positive results when subjected to the Molish's reaction, the Disch's reaction, the anthrone sulfuric acid reaction, the phenol sulfuric acid reaction, the tryptophane sulfuric acid reaction, the Lowry-Folin reaction and the ninhydrin reaction after hydrochloric acid hydrolysis, and being a product produced by extracting *Coriolus versicolor* (Fr.) Quel. with an aqueous alkaline solution having a concentration within the range of from 0.01 to 2.0N at a temperature of from 50° C. to 100° C., neutralizing the resultant extract, and subjecting the resulting neutralized extract to ultrafiltration or reverse osmosis to remove substantially all polymer units having a molecular weight below about 5,000 therefrom where the tumor is sensitive to such polysaccharide.

3. A pharmaceutical composition suitable for inhibiting the growth of tumor cells in a patient suffering therefrom or for restoring the immune response in a patient afflicted with tumors, in a suitable dosage unit form, comprising:
 a therapeutically effective dosage of nitrogen-containing polysaccharide substantially free of units having a molecular weight below about 5,000; and a pharmaceutically acceptable carrier,
 said nitrogen-containing polysaccharide having a nitrogen content of from 3 to 8%, showing positive results when subjected to the Molish's reaction, the Disch's reaction, the anthrone sulfuric acid reaction, the phenol sulfuric acid reaction, the tryptophane sulfuric acid reaction, the Lowry-Folin reaction and the ninhydrin reaction after hydrochloric acid hydrolysis, and being a product produced by extracting *Coriolus versicolor* (Fr.) Quel. with an aqueous alkaline solution having a concentration within the range of from 0.01 to 2.0N at a temperature of from 50° C. to 100° C., neutralizing the resultant extract, and subjecting the resulting neutralized extract to ultra-filtration or reverse osmosis to remove substantially all polymer units having a molecular weight below about 5,000 therefrom where the tumor is sensitive to such polysaccharide.

* * * * *

UNITED STATES PATENT AND TRADEMARK OFFICE
CERTIFICATE OF CORRECTION

PATENT NO. : 4,851,395

DATED : July 25, 1989

INVENTOR(S) : Saburo UENO et al.

It is certified that error appears in the above-identified patent and that said Letters Patent is hereby corrected as shown below:

On the title page:

Item:[60], line 1, change "Jun. 25, 1985" to --Nov. 25, 1985--;

line 3, after "abandoned," insert --which is a continuation of

Ser. No. 324,830, Nov. 25, 1981, abandoned,--.

Signed and Sealed this

Twenty-ninth Day of June, 1993

Attest:

MICHAEL K. KIRK

*Attesting Officer*  *Acting Commissioner of Patents and Trademarks*